US008747896B2

(12) United States Patent
Costantini et al.

(10) Patent No.: US 8,747,896 B2
(45) Date of Patent: *Jun. 10, 2014

(54) MUCOSAL BIOADHESIVE SLOW RELEASE CARRIER FOR DELIVERING ACTIVE PRINCIPLES

(75) Inventors: Dominique Costantini, Paris (FR); Caroline Lemarchand, Paris (FR)

(73) Assignee: BioAlliance Pharma, Paris (FR)

( * ) Notice: Subject to any disclaimer, the term of this patent is extended or adjusted under 35 U.S.C. 154(b) by 72 days.

This patent is subject to a terminal disclaimer.

(21) Appl. No.: 13/565,653

(22) Filed: Aug. 2, 2012

(65) Prior Publication Data

US 2012/0329817 A1    Dec. 27, 2012

Related U.S. Application Data

(63) Continuation of application No. 12/225,470, filed as application No. PCT/IB2007/001662 on Mar. 23, 2007, now abandoned.

(30) Foreign Application Priority Data

Mar. 24, 2006    (EP) ..................................... 06290480

(51) Int. Cl.
| A61K 9/26 | (2006.01) |
| A61K 47/32 | (2006.01) |
| A61P 31/12 | (2006.01) |
| A61K 31/522 | (2006.01) |
| A61K 47/20 | (2006.01) |
| A61K 47/42 | (2006.01) |

(52) U.S. Cl.
USPC ........ 424/470; 514/772; 514/772.5; 514/775; 514/263.38

(58) Field of Classification Search
None
See application file for complete search history.

(56) References Cited

U.S. PATENT DOCUMENTS

| 4,724,141 A | 2/1988 | Schmidt |
| 4,792,452 A | 12/1988 | Howard |
| 4,849,229 A | 7/1989 | Gaylord |
| 4,873,080 A | 10/1989 | Brickl |
| 4,915,948 A | 4/1990 | Gallopo |
| 5,116,603 A | 5/1992 | Friedman |
| 5,160,737 A | 11/1992 | Friedman |
| 5,215,755 A * | 6/1993 | Roche et al. .................. 424/480 |
| 5,330,746 A | 7/1994 | Friedman |
| 5,362,498 A | 11/1994 | Aiache |
| 5,955,502 A | 9/1999 | Hansen |
| 5,985,319 A | 11/1999 | Embil |
| 6,042,847 A | 3/2000 | Kerc |
| 6,210,699 B1 | 4/2001 | Acharya |
| 6,303,147 B1 | 10/2001 | Gilis |
| 6,752,997 B2 | 6/2004 | Safadi |
| 6,916,485 B2 | 7/2005 | Aiache |
| 7,651,698 B2 | 1/2010 | Aiache |
| 8,211,466 B2 | 7/2012 | Costantini |
| 2002/0103181 A1 | 8/2002 | Sen |
| 2003/0096791 A1* | 5/2003 | Gupte et al. .................... 514/57 |
| 2003/0108603 A1* | 6/2003 | Aiache et al. ................. 424/465 |

FOREIGN PATENT DOCUMENTS

| EP | 0 095 944 A2 | 7/1983 |
| EP | 0 542 824 A1 | 5/1993 |
| WO | WO-92/02209 | 2/1992 |
| WO | WO-97/15296 | 5/1997 |
| WO | WO-97/16174 | 5/1997 |
| WO | WO-98/47499 | 10/1998 |
| WO | WO-00/16751 | 3/2000 |

OTHER PUBLICATIONS

Bouckaert et al., 1992, "Comparison of Salivary Miconazole Concentrations After Administration of a Bioadhesive Slow-Release Buccal Tablet and an Oral Gel," *Eur J Clin Pharmacol.* 43(2):137-140.

Buckton, G., 1991, "The influence of surfactants on drug release from acrylic matrices," *Int. J. Pharm.*, 74:169-174.

Cardot et al., 2004, "Comparison of the Pharmacokinetics of Miconazole After Administration via a Bioadhesive Slow Release Tablet and an Oral Gel to Healthy Male and Female Subjects", 58(4):345-51.

Clarkson et al., 2000, "Interventions for preventing oral mucositis or oral candidiasis for patients with cancer receiving chemotherapy (excluding head and neck cancer)," *Cochrane Review Abstract.* 3:CD000978.

De Vries, 1991, "Developments in buccal drug delivery," *Crit Rev Ther Drug Carrier Syst.* 8(3):271-303.

Final Office Action mailed Oct. 24, 2011 for U.S. Appl. No. 11/715,967.

Freitage et al., 2003, "How do roll compaction/dry granulation affect the tableting behavior of inorganic materials? Comparison of four magnesium carbonates," *European Journal of Pharmaceutical Sciences* (19)281-289.

Greenspan et al., 1996, "HIV-related oral disease," *The Lancet,* 348:729-733.

(Continued)

*Primary Examiner* — Patricia A Duffy
*Assistant Examiner* — Garen Gotfredson
(74) *Attorney, Agent, or Firm* — Dechert LLP (57) ABSTRACT

A mucosal bioadhesive slow release carrier comprising an active principle and devoid of starch, lactose, which can release the active principal for a duration of longer than 20 hours. This bioadhesive carrier contains a diluent, an alkali metal alkylsulfate, a binding agent, at least one bioadhesive polymer and at least one sustained release polymer, as well as a method for its preparation.

28 Claims, 7 Drawing Sheets

(56) References Cited

OTHER PUBLICATIONS

Hermant et al., 1997, "Activité fongicide in vitro de différents bains de bouche sur la flore fongique gingivale de patients infectés par le VIH," *Med Mal Infect.* 27:715-718.

Hull et al., 2006, "Single-dose Famciclovir for the Treatment of Herpes Labialis," *Current Medical Research and Opinion* 22(9):1699-1702.

Imam et al., 1990, "Hierarchical Pattern of Mucosal *Candida* Infections in HIV-Seropositive Women," *The American Journal of Medicine,* 89:142-146.

Kovacs et al., 2000, "Prophylaxis against Opportunistic Infections in Patients with Human Immunodeficiency Virus Infection," *The New England Journal of Medicine,* 342(19):1416-1429.

Levy et al., 1963, "Effect of Certain Tablet Formulation Factors on Dissolution Rate of the Active Ingredient III", *J. of Pharmaceutical Sciences* 52(12):1139-1144.

Martin-Algarra et al., 1994, "Effects of Surfactants on Amiodarone Intestinal Absorption. I. Sodium Laurylsulfate," *Pharm. Res.,* 11(7):1042-1047.

Non-Final Office Action for U.S. Appl. No. 11/715,967 mailed Feb. 16, 2011.

Non-Final Office Action for U.S. Appl. No. 12/225,470 mailed Aug. 2, 2011.

Odds, 1981, "Persistence of Miconazole in Saliva after a Single Oral Dose," *J Clin Res Rev,* 1(3):231-232.

Office Action mailed Sep. 29, 2009 in Japanese counterpart application JP 2003-515193 (English language translation only).

PCT International Search Report from PCT/FR02/02635 dated Nov. 19, 2002.

Response to Cite No. C18 filed with the Japanese Patent Office on Mar. 25, 2010 (English language translation only).

Restriction Requirement Office Action for U.S. Appl. No. 12/225,470 mailed Aug. 2, 2011.

Rowe et al., 2012, "Handbook of Pharmaceutical Excipients," $7^{th}$ edn, London: *Pharmaceutical Press* 749-482.

Solubilities (http://www.pharminfotech.co.nz/manual/Formulation/mixtures/pages/solubilities.html).

Spruance et al., 2002, "Acyclovir Cream for Treatment of Herpes Simplex Labialis: Results of Two Randomized, Double-Blind, Vehicle-Controlled, Multicenter Clinical Trials," *Antimicrobial Agents and Chemotherapy* 46(7):2238-2243.

Summary of TIBOZOLE Product Characteristics from Tibotec Pharmaceuticals.

Vasquez, 1999, "Options for the Management of Mucosal Candidiasis in Patients with AIDS and HIV Infection," *Pharmacotherapy,* 19(1):76-87.

Veuillez et al., 2001, "Factors and strategies for improving buccal absorption of peptides," *European Journal of Pharmaceutics and Biopharmaceutics,* 51(2):93-109.

Weinert et al., 1996, "Oral Manifestations of HIV Infection," *Ann Intern Med.,* 125:485-496.

\* cited by examiner

MUCOSAL BIOADHESIVE SLOW RELEASE CARRIER FOR DELIVERING ACTIVE PRINCIPLES

CROSS REFERENCE TO RELATED APPLICATIONS

This application is a continuation of U.S. application Ser. No. 12/225,470, which is the U.S. national phase of international application no. PCT/IB32007/001662, filed Mar. 23, 2007, which claims the priority benefit of European application no. EP06290480.0, filed Mar. 24, 2006, the contents of all of which are incorporated herein in their entireties by reference thereto.

FIELD OF THE INVENTION

The present invention relates to a bioadhesive slow release carrier for the extended and controlled release of an active principle that can be used on mucosal surfaces. A process for manufacturing the bioadhesive system, a method for delivering an active ingredient to a mammal, as well as methods of treating, curing or preventing various medical conditions are also disclosed.

BACKGROUND OF THE INVENTION AND RELATED PRIOR ART

Mucous membranes are linings of ectodermic origin, covered in epithelium, and are involved in absorption and secretion. They line various body cavities that are exposed to the external environment as well as internal organs, such as the nostrils, the lips, the ears, the genital area, the digestive tract and the anus. Parts of the body featuring mucous membranes include most of the respiratory tract and the entire gastrointestinal tract, as well as the vagina, cervix, the clitoris, the covering of the glans penis and the inside of the prepuce. Many of the afore mentioned mucous membranes secrete mucus, which is a viscous colloid containing antiseptic enzymes such as lysozymes and immunoglobulins and is made up of mucins and inorganic salts suspended in water.

One of the problems associated with a bioadhesive drug delivery system for mucous membranes is that the lubricious nature of the mucous membranes allows for the active substance to be washed away or diluted lowering the drugs bioavailability such that the administered drug does not effectively treat the medical condition at hand. Another problem is that in the oral cavity, eating drinking and speaking and the constant replacement of the saliva often effects the delivery of the active substance.

Oral mucosa bioadhesive delivery systems are also well known in the art and are used to treat various medical conditions. These delivery systems are generally made of water soluble carbomers or insoluble polymers that can contain maize starch as a disintegrating agent and/or lactose as a diluent or binder. Generally the delivery of the active principle is over a period of less than 11 hours. Thus, in these drug delivery systems the carrier has to be replaced at least twice a day.

For instance, U.S. Pat. No. 5,643,603 describes a composition of a bioadhesive sustained delivery carrier for drug administration, which composition is made up of a mixture of pregalatinized starch and a synthetic polymer such as polyacrylic acid, hydroxyethyl cellulose, carboxymethyl cellulose, PVA, PVP and PEG (95%) and a drug (0.1 to 5%). This bioadhesive can be adhered to the mucosa or teeth and was deemed to deliver the drug over a period of seven hours.

Another form of a bioadhesive tablet is described in U.S. Pat. No. 6,248,358 in which the active ingredient is protected from water and the surrounding environment. This tablet contains 5 to 50% by weight hydroxypropyl methyl cellulose, 0.5 to 25% by weight corn starch, 1 to 50% by weight lactose, 0.5 to 10% by weight water insoluble cross-linked polycarbophil and 1 to 75% by weight carbomer or carbomer 974P. This hydrated sustained release tablet can deliver the active ingredient to the bloodstream via the patient's vaginal or buccal cavity.

A bioadhesive solid dosage form is described in U.S. Pat. No. 6,303,147, which has 0.001 to 10% of an active ingredient, 80 to 98% of pregelatinized starch, 1 to 10% of a hydrophilic matrix forming polymer such as polyacrylic acid, carbomer, hydroxyethyl cellulose, HPMC, carboxymethylcellulose, PVA or mixtures of these hydrophilic polymers, 0.2 to 5% of sodium stearyl fumarate and 0 to 1% of a glidant. It can be used for buccal, nasal, rectal or vaginal administration. The adhesion time of these tablets is about nine hours.

U.S. Pat. No. 6,916,485 describes a prolonged release bioadhesive therapeutic system containing 10 to 2,000 mg active ingredient 50% by weight natural proteins, at least 20% by weight of milk protein concentrate, 10 to 20% by weight of a hydrophilic polymer, a compression excipient such as corn starch, lactose or polyol and 3.5 to 10% by weight alkali metal alkylsulfate. This system is a mucoadhesive tablet for delivery to the mucosa.

All of the above issued patents use corn starch as a disintegrating agent or agents which plays a role in the prolonged release of the active ingredient. Also all of these patents disclose the use of lactose as a diluent or as a binding agent in their formulations. U.S. Pat. Nos. 5,643,603, 6,303,147 and 6,916,485 disclose the delivery of the active principle between 7 to 13 hours.

However, many people are lactose intolerant or are allergic to corn. Therefore, mucosal delivery systems containing lactose or corn are impossible to use by this population of people.

Moreover, in many of the above-mentioned slow release bioadhesive systems, the formulation of low aqueous soluble or insoluble active principles is difficult. Various categories of medicinal agents such as antivirals, analgesics, anti-inflammatories, antibiotics and antiseptics have members, which are hard to formulate and administer due to their low aqueous solubility or insolubility. An example of an antiseptic with low aqueous solubility is iodine, which crystallizes when placed in water. Another example of an insoluble analgesic that is difficult to formulate is fentanyl base. Numerous antiviral and immunosuppressive agents such as acyclovir are also difficult to formulate, have poor percutaneous penetration and have complications arising due to intramuscular administration at a strongly alkaline pH of 10-11.

For instance, the oral absorption of acyclovir is highly variable with a bioavailability ranging from 15% and 30%. In patients the systemic treatment regimen is 200 mg tablets, five times a day. Moreover, after systemic administration of acyclovir orally, peak acyclovir concentrations are found in saliva at the lower end of the 50% inhibitory dose of herpes simplex-1 virus. Local treatment of acyclovir as a cream is also poor due to poor percutaneous absorption. This cream must be applied at least 5 times a day over a period of 5 days.

Patients being treated for malignant diseases or HIV have further oral complications associated with their particular disease, due to immunosuppression. For instance, some of the most common oral manifestations in people who are infected with AIDS include bacterial infections such as gingivo-periodontal disease, fungal infections such as Candidiasis, viral infections such as Epstein-Barr virus, oral hairy leukoplakia, herpes simplex-1 virus, variacella-Zoster virus, human papilloma virus, cytomegalovirus, neoplasms such as Kaposi's sarcoma and lymphoma and other oral lesions including oral ulcers and salivary gland enlargement. Oral pain may be associated with each one of these complications.

Likewise, people undergoing chemotherapy and head/neck radiation also have oral complications including mucositis, infection, salivary gland dysfunction, taste dysfunction, viral, fungal and bacterial infections, xerostomia and gastrointestinal mucositis caused by the secondary modifications in the oral cavity. In about 40% of patients undergoing chemotherapy ulcerative oral mucositis occurs, in patients undergoing neck irradiation ulcerative oral mucositis occurs in almost every case.

Therefore, there is a need to accommodate multiple drugs treating different; medical complications in a single drug delivery system to avoid multiple administration of different medicaments.

Furthermore, when many of the drugs are administered to treat the oral complications, they have to be administered very frequently since they are generally released from the bioadhesive delivery system over a period of time from about 7 to 13 hours. The bioadhesive delivery system thus has to be changed frequently, which can result in added burden to the mammal receiving such treatment.

Thus, there are problems associated in the prior art for mucosal delivery that can deliver the active principle to treat various medical complications over a long period of time and more specifically greater than 20 hours. Furthermore there are problems also associated with the prior art with respect to the delivery of active principles, which have low aqueous solubility or are insoluble. Moreover, there is a need in the art to diminish taking multiple drugs to treat different medical conditions.

Therefore it is an object of the present invention to overcome the deficiencies in the prior art bioadhesive delivery systems.

It is an object of the present invention to provide a bioadhesive slow release carrier for mucosal delivery of an active ingredient for at least 20 hours duration.

It is another object of the present invention to provide a bioadhesive slow release carrier for mucosal delivery of a soluble or insoluble active principle.

It is yet another object of the present invention to provide a mucosal delivery bioadhesive slow release carrier in which the active principle can be administered once a day.

Another object if the present invention is to provide a mucosal bioadhesive slow release carrier in which the active principle can be liberated immediately and then liberated over a prolonged period of time of greater than 20 hours.

It is yet another object of the present invention to provide a mucosal bioadhesive slow release carrier that can contain at least two different active principles.

It is yet another object of the present invention to provide a process for manufacturing a mucosal bioadhesive slow release carrier without lactose or corn starch.

It is another object of the present invention to provide a process for manufacturing a mucosal bioadhesive slow release carrier that can deliver a soluble or insoluble active principle.

Yet another object of the present invention is a method for delivering an active principle to a mammal, especially mammals that are immunodepressed.

Methods of treating, curing or preventing various medical conditions and diseases are also objects of the present invention.

Methods of treating, curing or preventing mucosal diseases such as buccal diseases are also objects of the present invention.

Use of the mucosal bioadhesive slow release carrier for the manufacture of medicaments to treat, cure or prevent certain diseases is also an object of the present invention.

These and other objects are achieved by the present invention as evidenced by the summary of the invention, description of the preferred embodiments and the claims.

SUMMARY OF THE INVENTION

The present invention provides a mucosal bioadhesive slow release carrier comprising a wetting agent comprising at least one active principle comprising 1 to 75% by weight of a diluent, and 1 to 10% by weight of an alkali metal alkylsulfate, and further comprising 0.5 to 5% by weight of a binding agent and 5 to 80% by weight of at least one bioadhesive polymer selected from the group of natural polymers wherein said natural polymers are polysaccharides or, natural proteins from animal origin or vegetable origin or synthetic polymers, and mixtures thereof and 5% to 80% by weight of at least one polymer that provides a sustained release of the active principle.

The at least one polysaccharide that can be used in the present invention include chitosan, alginate, carboxymethyl cellulose, hydroxypropyl methyl cellulose, hydroxyethyl cellulose, hydroxypropyl cellulose, cyclodextrin, sodium hyaluronate and xanthum gum.

The at least one natural protein from vegetable origin or animal origin that can be used in the present invention include natural milk protein, natural pea protein, natural soy protein, natural potato protein, natural wheat protein and gliadin protein.

The at least one synthetic polymer that can be used in the present invention include carbomer, polyvinylalcohol and acrylic polymers.

The at least one active principle that can be used in the present invention include analgesics, anaesthetics such as lidocain, antalgics, antiviral agents, anti-inflammatory agents, antiemetic agents, antibiotics and antiseptics. Two or more different active principles besides the ones mentioned above including antiviral agents with different spectrum than those described above, an antifungal agent and a salivary agent can also be formulated in the bioadhesive carrier of the present invention.

In another aspect the present invention also provides a method for preparing a mucosal bioadhesive slow release carrier comprising:

a) granulating a mixture of at least one active principle with an alkali metal alkylsulfate, a diluent and a binding agent;

b) blending said granulated mixture with at least one bioadhesive polymer, at least one sustained release polymer and at least one compression agent; and c) compressing the blended mixture obtained in b).

In yet another aspect the present invention provides a method for delivering an active principle to a mammal, said method comprising mucosally administering to a mammal in need of said active principle, a bioadhesive slow release carrier comprising a wetting agent comprising at least one active principle, 1 to 75% by weight of a diluent and 1 to 10% by weight of an alkali metal alkylsulfate and further comprising 0.5 to 5% by weight of a binding agent and 5 to 80% by weight of at least one bioadhesive polymer selected from the group of natural polymers wherein said natural polymers are polysaccharides or, natural proteins from animal origin or vegetable origin or synthetic polymers, and mixtures thereof and 5 to 80% by weight of at least one polymer that provides a sustained release of the active principle.

Methods of alleviating, treating, preventing or curing various medical conditions also are a part of the present invention. Thus, medical conditions or diseases such as orofacial herpes-herpes simplex virus 1 (HSV-1), genital herpes-herpes simplex virus 2 (HSV-2), oral mucositis, fungal infections such as Candidiasis, viral infections such as Epstein-Barr virus, oral hairy leukoplakia, variacella-Zoster virus, human papilloma virus, cytomegalovirus, Kaposi's sarcoma due to human herpes V8 and genital warts due to human papilloma virus and other oral lesions including oral ulcers and salivary gland disturbance, altered oral flora (decreased bacterial flora), taste dysfunction, periodontitis, xerostomia (salivary gland dysfunction), gastrointestinal mucositis causing secondary changes in oral status including inflammation, hygiene and dietary intact and oral pain can be treated using the mucosal bioadhesive slow release carrier of the present invention.

The methods of alleviating, treating, preventing or curing the above medical conditions using the mucosal bioadhesive slow release carrier of the present invention can be used to treat immunocompromised mammals.

Use of the mucosal bioadhesive slow release carrier of the present invention for the manufacture of a medicament to alleviate, treat, prevent or cure mucosal diseases or buccal diseases or genital diseases is also provided in the present invention.

DESCRIPTION OF THE PREFERRED
EMBODIMENTS OF THE INVENTION

As used herein the term "mucosal" encompasses oral/buccal, vaginal, esophageal, nasal and rectal delivery.

The term "bioadhesive" refers to any adhesive that interfaces with living tissue and/or biological fluid.

By the term "carrier" is meant any object that can transport at least one active principle.

As used herein the term "active principle", "drug" and "active ingredient" are used interchangeably. The active principle is used to alleviate, treat or prevent a medical condition or disease. In some instances the active principle can be used to cure a medical condition or disease.

"Medical condition" and "disease" are also used interchangeably herein and refer to any condition in a mammal or one of its parts that impairs normal functioning in the mammal. This impairment may lead to illness or sickness characterized by certain symptoms and physical findings suffered by a mammal.

The term "mammal" encompasses any of various warm-blooded vertebrate animals of the class Mammalia, including humans, characterized by a covering of hair on the skin and, in the female, milk-producing mammary glands for nourishing the young.

As used herein the term "buccal" means of, relating to, involving or lying in the mouth.

As used herein the term "diluent" means a diluting agent and encompasses such agents that are insoluble diluents and soluble diluents.

The term "binder" when used herein relates to any pharmaceutically acceptable film which can be used to bind together the active and inert components of the carrier together to maintain cohesive and discrete portions. Binders provide the matrix from which the active principle is gradually secreted.

As used herein, the expression "residence time" will refer to the time for which the carrier placed on the target mucosal surface will remain substantially intact.

Similarly, throughout the text the expression "slow release" or "sustained release" are used interchangeably and mean that the active principle is released immediately after 30 minutes and then over a prolonged period of time of at least 15 hours or at least 18 hours or at least 20 hours or at least 24 hours and up to 36 hours.

By the term "insoluble" when referring to the active principle means that the drug can be totally insoluble in an aqueous medium or has limited solubility in an aqueous medium.

By "limited solubility" is meant that the active principle has a solubility below 10 mg/ml in 250 ml of water over a pH range from 1.0 to 7.5. Classes of drugs that can have "limited solubility" are those drugs that are hydrophobic or those which are classified in the Biopharmaceutical Classication System (BCS) as being type III or type IV drugs.

More specifically, the present invention relates to a mucosal bioadhesive slow release carrier that can deliver an active principle over a period of time of at least 20 hours and up to 36 hours. More specifically the active principle can be delivered from 30 minutes to 15 hours, 30 minutes to 18 hours, 30 minutes to 20 hours or 30 minutes to 24 hours or 30 minutes to 36 hours. Thus, this carrier has the advantage that it provides an effective residence time for the active principle such that only a single daily dosage is necessary.

Moreover, due to its increased bioavailability of the active principle, a reduced dosage of active principle is feasible using this drug delivery system since, as evidenced in the Examples, the delivery of the active principle is higher than the minimum inhibitory concentration over a prolonged period of time.

More specifically, the bioadhesive slow release carrier of the invention can be used for preventing, alleviating, curing or treating mucosal diseases, buccal, oesophageal or vaginal infections in mammals.

Still more specifically, bioadhesive slow release carrier of the invention can be used for preventing, alleviating, curing or treating buccal herpes simplex 1 (HSV-1) infections, especially in immunodepressed mammals such as those mammals that have AIDS or SIV or have been subjected to chemotherapy or radiation therapy.

The present invention is not limited to treating only humans, but also encompasses veterinary applications, especially since it is well known that animals also can have oral medical completions.

The process to formulate the bioadhesive slow release carrier of the present invention permits the use of an active principle, which can be soluble, insoluble or having limited solubility in an aqueous solution such as water. It is known in the art that insoluble or limited solubility drugs pose problems in their formulation and there is limited choice for a delivery system. In many delivery systems there is decreased bioavailability of the active principle, incomplete release from the dosage form and higher interpatient variation. Thus, in many instances the active principle must administered more frequently and monitored more closely. The present invention overcomes these difficulties.

The carrier of the present invention can be in the form of a tablet, microspheres and the like. They can be formulated in any shape such as rectangular, circular, square, oval and the like. It should be appreciated that the dimensions of the carrier depend on the delivery mode that is used. For example, for gingival delivery, the carrier has a flat surface and a curved surface. The carrier can also be coated with an active principle described hereafter.

The mucosal bioadhesive stew release carrier of the present invention comprises at least one active principle, a diluent, an alkali metal alkylsulfate, a binding agent, at least one bioadhesive polymer and at least one polymer that provides sustained release of the active principle.

More specifically, mucosal bioadhesive slow release carrier comprises a wetting agent comprising at least one active principle, 1 to 75% by weight of a diluent and 1 to 10% by weight of an alkali metal alkylsulfate and further comprising 0.5 to 5% by weight of a binding agent and 5 to 80% by weight of at least one bioadhesive polymer selected from the group of natural polymers wherein said natural polymers are polysaccharides or natural proteins from animal origin or vegetable origin or synthetic polymers and mixtures thereof and 5% to 80% by weight of at least one polymer that provides a sustained release of the active principle.

The at least one polysaccharides that can be used in the present invention include for example chitosan, alginate, carboxymethyl cellulose, hydroxypropyl methyl cellulose, hydroxyethyl cellulose, hydroxypropyl cellulose, sodium hyaluronate, cyclodextrin and xanthum gum.

The at least one natural protein from vegetable origin or animal origin that can be used in the present invention include natural milk protein, natural pea protein, natural soy protein, natural potato protein, natural wheat protein and gliadin protein.

The at least one synthetic polymer that can be used in the present invention include carbomer, polyvinylalcohol and acrylic polymers.

More specifically, the active principle which is incorporated into the bioadhesive slow release carrier includes antiviral agents, antifungals, analgesics, anaesthetics, antalgics, anti-inflammatory agents, antiemetics, antibiotics and antiseptics. More than one active principle can be used depending on the needed application. For example, one can envision treating herpes simplex 1 using an antiviral such as acyclovir, as well as an anti-inflammatory for pain in the same bioadhesive carrier.

Examples of antiviral agents that can be used in the bioadhesive carrier include, for example, vidarbine, acyclovir, ganciclovir, ciclovir, valganciclovir, nucleoside analog reverse transcriptase inhibitors such as zidovudine, didanosine, zalcitabine, stavudine, lamivudine, non-nucleoside reverse transcriptase inhibitors such as nevirapine and delavridine, protease inhibitors such as saquinavir, ritonavir, indinavir, nelfinavir, ribavirin, amantadine, rimantadine, releenza, tamiflu, pleconatil, penciclovir, famciclovir, foscamet, interferons such as IFN-α and the like.

The antiviral agent is present in the bioadhesive carrier in a concentration between 10 to 200 mg. It can also be present in a concentration between 50 to 100 mg. It will be appreciated that the amount of the antiviral can vary depending on the mammal being treated as well as the medical condition of the mammal.

Examples of antifungal agents that can be used in the bioadhesive carrier include, for example, polyene antimycotic and imidazole and triazole such as clotrimazole.

The dosage of antifungal varies in the bioadhesive carrier with the antifungal utilized. Generally the dose is between 10 mg to 150 mg.

Sulfa drugs and folic acid analogs, the beta-lactams including penicillins, vancomycin, ampicillin and amoxicillins and cephalosporins, aminoglycosides such as streptomycin, kanamycin, neomycin and gentamycin, tetracyclines such as doxycycline, macrolides, licosamides, streptogramins, fluoroquinolines such as ciprofloxacin, levofloxacin and moxifloxacin, polymixins, rifampin, mupirocin, cycloserine, aminocyclitols, glycopeptides and oxazolidinones are examples of antibiotics that can be used in the bioadhesive slow release carrier.

The dosage of antibiotic varies in the bioadhesive carrier with the antibiotic utilized. Generally the does is between 10 mg to 150 mg.

Examples of anti-inflammatory drugs that can be used in the bioadhesive carrier include aspirin, salsalate, diflunisal, ibuprofen, ketoprofen, nabumetone, piroxicam, naproxen, diclofenac, indomethacin, sulindac, tolmetin, etodolac, ketorolac, oxaprozin, trisalkylate, acetaminophen, suprofen, corticoids, celecoxib and thalidomide.

The dose of the anti-inflammatory present in the bioadhesive slow release carrier is between 25 and 1,500 mg or between 50 and 500 mg depending on the anti-inflammatory utilized.

Sodium laurylsulfate, iodophore, iodine, chlorhexidine gluconate, quaternary ammonium compounds such as cetylpyridinium chloride, phenolic antiseptics such as Listerine®, povidone-iodine, hexetidine, triclosan, deimopinol, salifluor, sanguinarine, alkali metal akylsulfates and propolis are antiseptics that can be used in the present invention.

Between 0 to 5% of the antiseptic is used in the bioadhesive carrier of the invention.

Antiemetic drugs that can be used to treat nausea and vomiting, especially after chemotherapy include granisetron, ondansetron, dexamethasone and metoclopramide, 5-hydroxytryptanine (serotonin) inhibitors, dronabinol and prochloperazine and tropisetron. These drugs and combinations thereof can be used in the bioadhesive carrier.

The antiemetic is generally present in a dose between 1 to 100 mg in the carrier.

Besides the active principle, the bioadhesive slow release carrier has an adhesive system, which allows the carrier to adhere to mucosal surfaces over a prolonged period of time.

The adhesive system comprises a diluent, an alkali metal alkysulfate, a binding agent, at least one bioadhesive polymer and at least one sustained release polymer.

The diluent used in the present invention can be insoluble or soluble. The diluent used is insoluble when the active principle is soluble and the diluent is soluble when the active principle is insoluble.

Examples of insoluble diluents include microcrystalline cellulose, silicified microcrystalline cellulose, hydroxymethylcellulose, dicalcium phosphate, calcium carbonate, calcium sulfate, magnesium carbonate, tricalcium phosphate and the like.

Examples of soluble diluents include mannitol, glucose, sorbitol, maltose dextrates, dextrins, dextrose and the like.

The diluent is present in an amount between 1 and 75% by weight in the bioadhesive slow release carrier.

An alkali metal alkylsulfate is also a component of the bioadhesive carrier of the present invention. This alkali metal sulfate increases the granulation of the active principle acting as a solubilization agent. The alkali metal alkylsulfate that can be used in the formulation includes magnesium lauryl sulfate, potassium lauryl sulfate, sodium laurylsulfate and diethylsulphosuccinate. Generally it is present in the bioadhesive carrier at a concentration of between 1 to 10% by weight or 2 to 10% by weight.

The mucosal bioadhesive slow release carrier used in the present invention permits the immediate local liberation of the active principle, as well as the prolonged liberation of the active principle.

The binders used in the present invention can be selected from carboxy vinyl polymer, methycellulose, hydroxyethylcellulose, hydroxypropyl cellulose, polyvinylpyrrolidone, polyethylene glycol and the like. The binders are present in the amount of 0.5 to 5% by weight in the bioadhesive slow release carrier.

The bioadhesive polymers are selected from the group of natural polymers, polysaccharides, chitosan, alginate, carboxymethyl cellulose, hydroxypropyl methyl cellulose, hydroxyethyl cellulose, hydroxypropyl cellulose, cyclodextrin, sodium hyaluronate, xanthum gum, natural proteins from animal origin or vegetable origin, natural milk proteins, natural pea proteins, natural soy proteins, natural potato proteins, natural wheat proteins, gliadin proteins, synthetic polymers, carbomer, polyvinylalcohol, acrylic polymers and mixtures thereof.

They are present in the bioadhesive carrier at a concentration of 5 to 80% by weight. The can also be present in an amount of 10% to 40% by weight.

Regarding the natural milk proteins, these are described in EP 0 542 824. They can be obtained from pasteurized raw milk and include total milk proteins, casein protein concentrates and whey protein concentrates.

The total milk proteins are recovered from skimmed milk after ultrafiltration. The casein protein products are obtained by insolubilizing the casein in milk at its isoelectric point, and further washing and drying the casein. The whey protein concentrates are obtained after coagulating cheese with enzymes and separating the yellow-green liquid residue out, which residue is whey. The whey is then further concentrated by ultrafiltration, ion exchange chromatography or thermal precipitation.

Example of milk proteins are those titrating a minimum of 85% proteins such as Prosobel L85, 1180, 1380 or 1395 or Promilk852A sold by Armor Proteins or from the Alaplex range (4850, 1180, 1380 or 1395) from NZMP (Paris, France).

Regarding the vegetable proteins, they can be obtained from pea, soy, potato, wheat or gliadin. The method for producing pea protein is described in WO 2007/017571.

Example of pea proteins are those titrating a minimum of 85% proteins such as Nutralys® sold by Roquette (France).

The sustained release polymers that can be used in the bioadhesive carrier include hydrophilic polymers including polysaccharides such as cellulose ethers, xanthum gum, scleroglucan, locust bean gum, gum Arabic gum tragacanth, carob, alginic acid, alginates, carrageenates, agar-agar and guar gum either alone or in mixtures thereof. Other polymers that can be used in the present invention include cellulose based polymers such as hydromellose, cellulose acetate, cellulose esters, cellobiose, cellulose resins atone or in mixtures thereof.

The sustained release polymers are present in a concentration of 5% to 80% by weight. They can also be present to an amount of 10% to 40% by weight.

The alkali metal alkylsulfate is present in a concentration of 1 to 10% by weight. They can also be present in an amount of 2% to 6% by weight.

Salivation agents such as pilocarpin and bethanechol and flavorings agents can also be added. Flavoring agents include calcium citrate, Safrole, and sweetening agents such as aspartame, cyclamates, saccharin and xylitol. Additionally compression excipients such as flow aids including talc, colloidal silicone dioxide, colloidal silica and lubricants including magnesium stearate, stearic acid, polyethylene glycol can also be added to the bioadhesive slow release carrier at the stage of blending.

These additional agents can be added to the carrier in the concentration range of 0.1 to 10% by weight of the total weight of the components in the carrier.

In one embodiment the bioadhesive slow release carriers are intended to prevent and treat HSV-1, HSV-2, varicella zoster virus (VZV), Epstein-Barr virus, human herpes virus 8, avian influenza, mumps, HIV, respiratory syncitial virus, influenza, parainfluenza and cytomegalovirus infections. A preferred active principle is a compound from the spectrum of nucleosides antivirals preferably selected from acyclovir, valacyclovir, ganciclovir or zidovudine. Thus in one aspect the nucleoside antiviral compound used in the bioadhesive is acyclovir, present in a dose of 10 to 200 mg per carrier.

In yet another embodiment the present invention relates to a mucosal bioadhesive slow release carrier comprising a wetting agent comprising 10 to 200 mg of an antiviral agent selected from the group of acyclovir, valacyclovir, gancyclovir and zidovudine, 1 to 75% by weight of a diluent of microcrystalline cellulose and 2 to 10% by weight of sodium lauryl sulphate and further comprising 0.5 to 5% by weight of a polyvinylpyrrolidine and 10 to 40% by weight of at least one bioadhesive polymer selected from the group of natural milk proteins and mixtures thereof and 10% to 40% by weight of hypromellose.

In addition, and especially in the case of treating two different medical conditions the active principle described above can be combined with an antiviral, an antifungal, an analgesic, an anaesthetic, an antalgic, an antiemetic, a salivation agent, an antiseptic, an anti-inflammatory, an antibiotic and mixtures thereof.

For example, if a patient has herpes simplex virus 1 and pain the combined use of acyclovir with an analgesic such as ibuprofen is particularly advantageous since HSV-1 infection is sometimes accompanied by labial or buccal pain.

Thus, the present invention provides a mucosal bioadhesive slow release carrier comprising a wetting agent comprising at least two active principles selected from the group of antiviral agents, analgesics, anaesthetics, antalgics, anti-inflammatory agents, antiemetics, antibiotics, antiseptics, an antiviral, an antifungal, a salvation agent, 1 to 75% by weight of a diluent and 1 to 10% by weight of an alkali metal alkylsulfate and further comprising 0.5 to 5% by weight of a binding agent and 5 to 80% by weight of at least one bioadhesive polymer selected from the group of natural polymers wherein said natural polymers are polysaccharides or natural proteins from animal origin or vegetable origin or synthetic polymers, and mixtures thereof and 5% to 80% by weight of at least one polymer that provides a sustained release of the active principle.

The combination of at least two active principles is also important in treating oral complications that arise from chemotherapy and head and neck radiation due to direct lethal and sublethal damage to oral tissues. Moreover, many patients have decreased immune systems, which lead to problems in the healing of oral tissues. Thus complications arising with patients undergoing chemotherapy and radiation treatment include oral mucositis, oral viral, bacterial and fungal infections, salivary gland dysfunctions altered oral flora, taste dysfunctions, xerostomia and gastrointestinal mucositis, which causes secondary changes in oral status including taste, hygiene and dietary intact. Gastrointestinal mucositis causes nausea and vomiting. These complications require treatment with more than one drug. For example, one can use the analgesic fentanyl base, fentanyl citrate or sulfentanyl which are important in treating severe resistant pain in particular associated with cancer, and an antiemetic to treat nausea and vomiting. It will be appreciated that the combinations of the different active principles utilized are based on the medical conditions that the patient/mammal has and the treatment that is necessary.

Hence the present invention provides a bioadhesive slow release carrier that can be used in the treatment of oral complications due to chemotherapy or radiation treatment comprising a wetting agent containing at least two active ingredients selected from the group of antiviral agents, analgesics, anaesthetics, antalgics, anti-inflammatory agents, antiemetics, antibiotics, antiseptics, an antiviral, an antifungal, a salivation agent 1 to 75% by weight of a diluent and 1 to 10% by weight of an alkali metal alkylsulfate and further comprising 0.5 to 5% by weight of a binding agent and 5 to 80% by weight of at least one bioadhesive polymer selected from the group of natural polymers wherein said natural polymers are polysaccharides or natural proteins from animal origin or vegetable origin or synthetic polymers, and mixtures thereof and 5% to 80% by weight of at least one polymer that provides a sustained release of the active principle.

The unique properties of the mucosal bioadhesive slow release carrier is due to its formulation. Generally the process of the present invention concerns using a wet granulation technique in its formulation.

In the methods of the prior art there is generally a wetting agent used such as lactose in the initial steps in the formulation process. In the process of the present invention lactose is not used. Rather, the combination of the active principle, diluent and alkali metal akylsulfate act as the wetting agent in the process.

In an aspect the present invention also provides a method for preparing a mucosal bioadhesive slow release carrier comprising:
a) granulating a mixture of at least one active principle with an alkali metal alkylsulfate, a diluent and a binding agent;
b) blending said granulated mixture with at least one bioadhesive polymer, at least one sustained release polymer and at least one compression agent; and
c) compressing the blended mixture obtained in b).

In another aspect, the present invention also relates to a method of preparing a bioadhesive carrier, the method comprising:
a) mixing at least one active principle with an alkali metal alkylsulfate and a diluent to form a mixture;
b) wetting said mixture with a binding agent;
c) drying and calibrating said mixture;
d) granulating said mixture to form primary granules;
e) blending said primary granules with at least one bioadhesive polymer and at least one sustained release polymer and at least one compression agent; and
f) compressing the blended mixture obtained in e).

More specifically, the active principle, the diluent and the alkali metal alkylsulfate are first individually weighed, sieved and premixed in a blender. The binding agent is weighed and solubilized using purified water. The solubilized binding agent is then added to the mixture containing the active ingredient and stirred form a wet granulation. The mixture is granulated using a suitable pharmaceutical mixer or granulator such as a planetary mixer or a high sear mixer then dried and calibrated.

The bioadhesive polymer, the sustained release polymer and compression excipients are then weighed and sieved. These ingredients were then added to the primary granulated mixture to form a final blending mixture, which was then further compressed using a suitable tablet press such as a rotative press.

The active principle that can be used in the method of the present invention are described above, as well as the particular diluents, binding agents, alkali metal alkylsulfates, bioadhesive polymers and sustained release polymers used in the present method.

In another embodiment the present invention provides a method of preparing a bioadhesive carrier, the method comprising:
a) mixing at least one active principle selected from:
an antiviral, an analgesic an anti-inflammatory, an antibiotic, an antiseptic, an antiemetic and mixtures thereof with 1 to 10% by weight of an alkali metal alkylsulfate and 1 to 75% by weight of a diluent;
b) wetting said mixture with 0.5 to 5% by weight binding agent that has been solubilized;
c) drying and calibrating said mixture;
d) granulating said mixture to form primary granules;
e) blending said primary granules with 5 to 80% by weight of at least one bioadhesive polymer selected from the group of natural polymers such as polysaccharides or natural proteins from animal origin or vegetable origin or synthetic polymers, and mixtures thereof and 5% to 80% by weight of at least one polymer that provides a sustained release of the active principle and at least one compression agent; and
f) compressing the blended mixture obtained in e).

In yet another aspect the present invention relates to the use of the mucosal bioadhesive slow release carrier according to the present invention for the manufacture of a medicament to treat mucosal diseases.

In this respect the mucosal diseases can be buccal diseases including herpes simplex virus 1 (HSV-1), herpes simplex virus (HSV-2), oral mucositis, oral Candidiasis, oral hairy leukoplakia, oral ulcers, salivary gland disturbance, altered oral flora (decreased bacterial flora), taste dysfunction, periodontitis, xerostomia, gastrointestinal mucositis causing secondary changes in oral status including inflammation, hygiene and dietary intact and oral pain. These diseases can be treated with at least one active principle or at least two different active principles.

In yet another aspect of the present invention, the mucosal diseases can be genital diseases including herpes simplex virus 2 (HSV-2), herpes simplex virus 1 (HSV-1) or human papilloma virus. These diseases can be treated with at toast one active principle or at least two different active principles.

In yet another aspect the present invention relates to the use of the mucosal bioadhesive slow release carrier according to the invention for the manufacture of a medicament to treat herpes simplex virus 1 (HSV-1), herpes simplex virus 2 (HSV-2) Epstein-Barr virus, human papilloma virus, cytomegalovirus, variacella-Zoster virus, Kaposi's sarcoma due to human herpes V8 and genital warts due to human papilloma virus.

In another aspect the present invention provides a method of delivering at least one active principle to a mammal in need of said active principle comprising administering the bioadhesive slow release carrier of the present invention, which is described in detail above.

In yet another aspect, the present invention provides a method of treating a mucosal disease in a mammal in need of such treatment, said method comprising administering the bioadhesive slow release carrier of the present invention, which is described in detail above. The mucosal diseases are described above.

A number of embodiments of the invention have been described. Nevertheless, it will be understood that various modifications may be made without departing from the spirit and scope of the invention.

EXAMPLES

Example 1

Preparation of the Bioadhesive Slow Release Carrier of the Present Invention 100 mg of acyclovir, 15% by weight microcrystalline cellulose and 4.5% by weight of sodium lauryl sulfate were weighed and sieved with a 0.7 to 2 mm sieve before premixing in a blender to provide the "initial mix."

At the same time, 0.4% by weight polyvinylpyrrolidone was dissolved in purified water. The resulting solution was added to the initial mix and further stirred. The wetted mixture was then granulated using a pharmaceutical mixer or granulator such as a planetary mixer or high sear mixer and dried and then calibrated to 500 µm. The resulting pellets formed the "primary granules."

20% milk concentrate protein, 15% hypromellose, 1% magnesium stearate and 0.4% of colloidal silica were weighed and sieved using a 500 µm sieve. These ingredients were then added to the primary granulation to form the "final blending" mixture. The final blending mixture was then compressed using a tablet press such as a rotative press to produce the compressed carriers according to the invention.

The size of the tablets was about 10 mm in diameter. The dimension was chosen to be comfortable in the canine fossa.

The above-described method was suitable for the production of compressed carrier batches ranging from 2 to 23 kg.

Example 2

Particle Size Distribution of the Primary Granules

Figure 1:
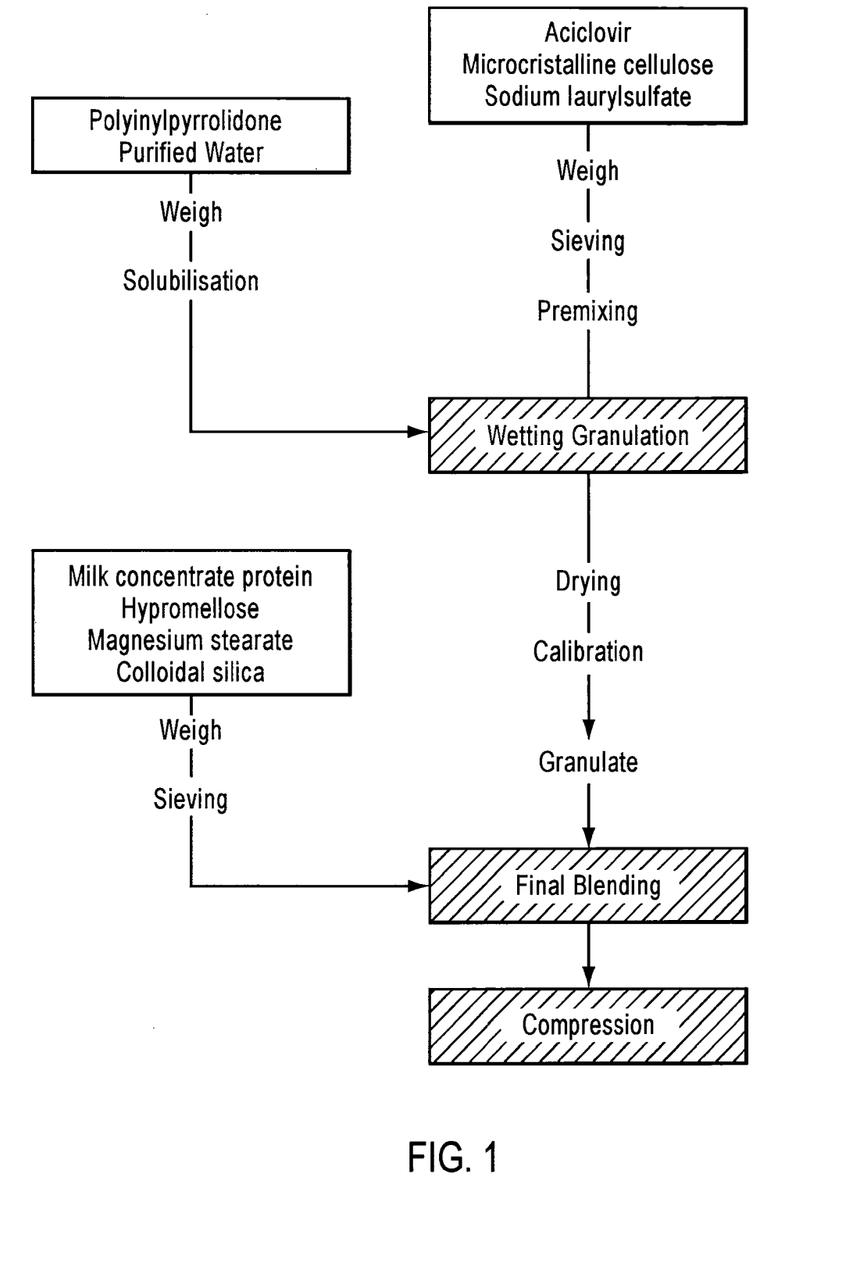
FIG. 1 is a schematic representation of the process of the present invention.

The primary granules obtained from the procedure in Example 1, after granulating, drying and calibrating, were then evaluated by sieve analysts based on the procedure described in the European Pharmacopoeia. Also an analysis was undertaken to determine the content of acyclovir in the different fractions of the granulations or in the whole granule. The acyclovir content in the granule was assayed using phosphate buffer at pH 6. Two different formulations were compared. The first formulation corresponded to those obtained in Example 1 of the present invention, while the "control formulation" was that disclosed in U.S. Pat. No. 6,916,485, to obtain the "primary grain" set forth in FIG. 1 therein.

Figure 2:
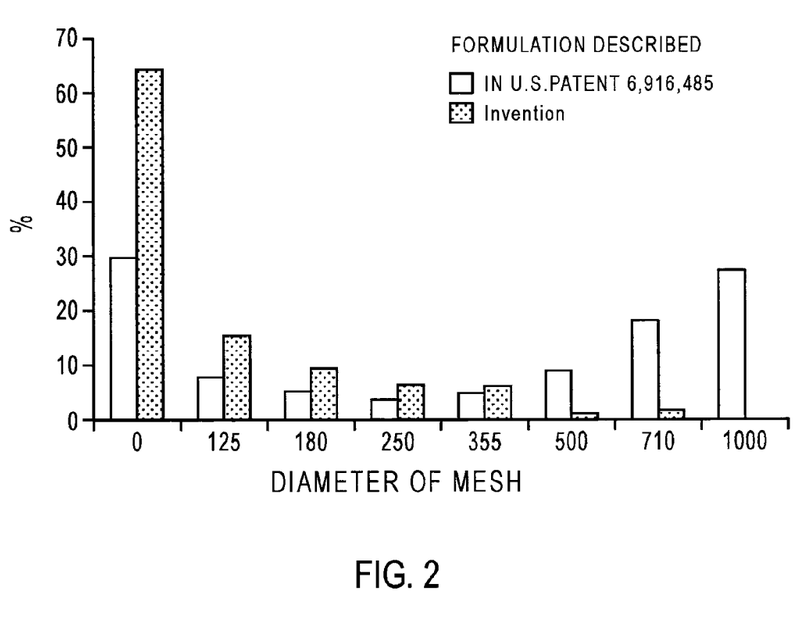
FIG. 2 is graph showing the diameter of mesh of the graded sizes obtained from the formulation of the present invention compared to the formulation described in U.S. Pat. No. 6,916,485.

The results are presented in FIG. 2. When granulations were prepared according to the formulation described in U.S. Pat. No. 6,916,485 (white bars), the size distribution of the granules reveals a strong heterogeneity, with the presence of two predominant extreme populations with a granule diameter of greater than 1000 µm or less than 125 µm, respectively. It further appeared that the acyclovir content of the granules having a size distribution of less than 125 µm granules is under-dosed.

To the contrary, when the granules were prepared according to the method of the present invention (dark bars in FIG. 2), the predominant fraction of granules had a diameter of less than 125 µm. The size distribution is homogeneous with that of the excipients that were added in the external phase. Further, the flow properties of the granules made according to Example 1 above were totally compatible with the compression step, and the final blending possessed a very good compression ability. Finally, the resulting granules of the present invention contained 100% of the desired acyclovir content, as well as the corresponding compressed carrier, thereby demonstrating the homogeneity of the blending and the reliability of the fabrication process.

Example 3

In Vitro Evaluation of an Acyclovir Bioadhesive Slow Release Carrier

The bioadhesive slow release carriers obtained by the process described in Example 1 were tested for acyclovir release through a dissolution method. The test was conducted according to the current dissolution testing described in U.S. Pharmacopoeia, $23^{rd}$ edition, Chapter 711 (Dissolution) pages 1791-1793. More specifically, sample vessels were submerged in a water bath at 37° C., in a suitable dissolution medium of phosphate buffer at a pH of 6 and the content of the vessels were agitated using a "rotating basket" attached to a shaft that is also attached to another shaft. The solid bioadhesive slow release carriers of the present invention were placed in the medium filled vessel at time zero. The water bath was maintained at 37° C. throughout the experiment, as well as the mixing speed of 60 rpm. 1 ml aliquots were taken from the vessels every hour for the first eight hours, then at 10, 11, 12, 15 and 24 hours and the amount of acyclovir released in the dissolution medium was measured by HPLC.

Figure 3:
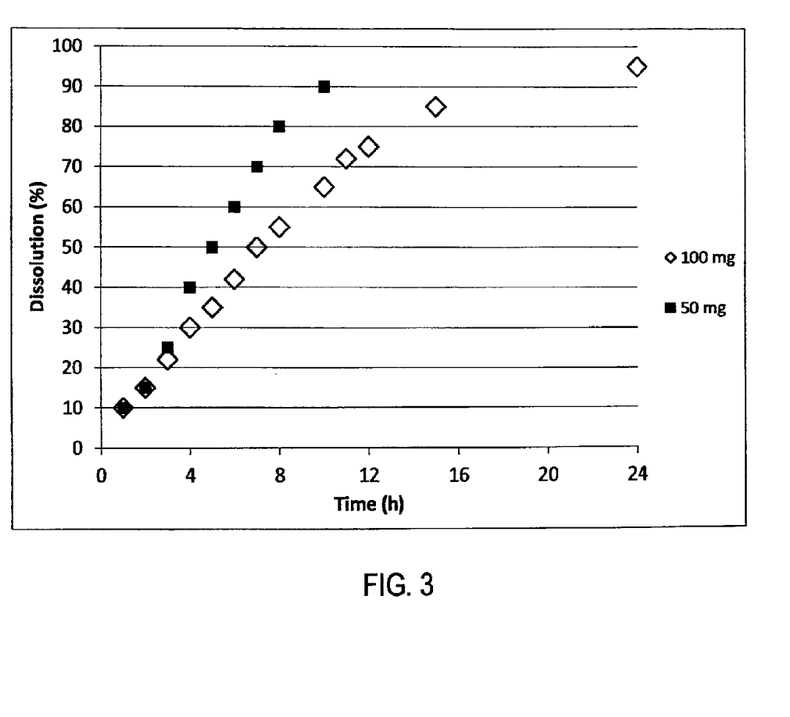
FIG. 3 is a graph showing the dissolution of acyclovir from the bioadhesive slow release carrier of the present invention over time in hours. 50 mg and 100 mg dosages were used.

The resulting dissolution profile is set forth in FIG. 3. As demonstrated in this graph, acyclovir released from the bioadhesive slow release carrier of the present invention is progressive and sustained during 24 hours, with a predominant amount of acyclovir (80%) released after 10 hours.

Example 4

Pharmacokinetics of the Acyclovir Bioadhesive Slow Release Carrier

The main goal of this pharmacokinetic study was to evaluate the systemic passage of the acyclovir following the application of the bioadhesive slow release carrier at the level of the canine fossa (upper gingiva) in healthy volunteers. Additional goals were to evaluate the loco-regional concentrations of acyclovir in the saliva, which represents a virus reservoir site, and at the labial level, which constitutes the expression site for an herpes simplex 1 infection.

In order to evaluate the absorption level of acyclovir through the new mode of administration of the present invention, data was obtained with the bioadhesive slow release carrier of the present invention and compared to oral administration of 200 mg acyclovir tablets. Further, to evaluate the therapeutic potential of the new bioadhesive slow release carriers of the present invention, plasma and loco-regional concentrations were compared to the minimal inhibitory concentration (MIC) of acyclovir towards HSV-1 virus, which is 22.5 ng/ml.

The study was undertaken using 12 healthy volunteers and was a monocentric, randomized, cross-over and open evaluation.

Two acyclovir bioadhesive slow release carriers synthesized according to Example 1 were tested, containing either 50 mg or 100 mg of acyclovir.

Plasma, salivary and labial (lip) samples were taken prior to the administration of the treatment, and then regularly at 24 hours, 36 hours and 48 hours after administration. Labial sampling was accomplished by utilizing a stripping method; i.e., an adhesive disk was used to collect the superficial cell layers of the lip. To avoid lip contamination with saliva, labial sampling was performed prior to saliva sampling after the lips were carefully wiped.

The acyclovir was then extracted and measured by HPLC. The quantification limit was set at 10 ng/ml for plasma and saliva samples, and at 6.5 ng/cm$^2$ for labial samples.

Example 5

Evaluation of the Acyclovir Systemic Transfer

Figure 4:
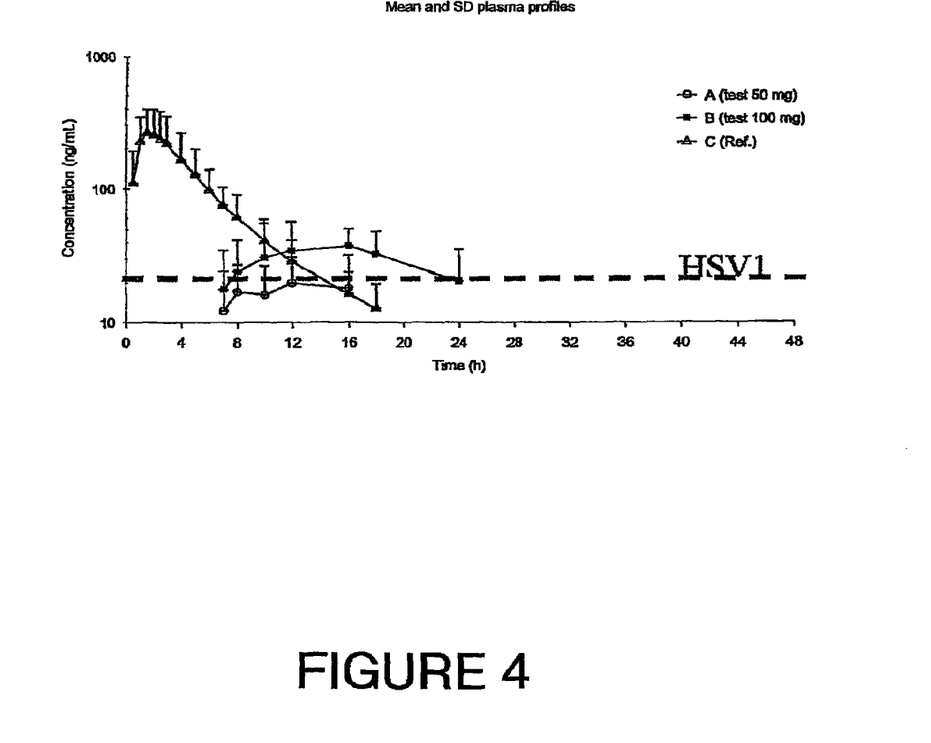
FIG. 4 is a graph showing the concentration acyclovir in the plasma over time in hours using the bioadhesive slow release carrier of the present invention compared with that of an oral acyclovir tablet.

The plasma concentration profiles are presented in FIG. 4.

The control tablet corresponding to the orally administered acyclovir exhibits an immediate-release profile, characterized by a rapid absorption phase, with a maximum concentration of 254 ng/ml at 1.5 hours. As seen in FIG. 4, the control tablet allows the plasma concentration of acyclovir to remain higher than the minimal inhibitory concentration (MIC) during 14 hours.

To the contrary, the acyclovir bioadhesive slow release carriers of the present invention exhibit a sustained-release profile with a 6 hour delay in the absorption of the acyclovir, and a maximum concentration of 45.9 µg/ml at 12 hours. After an increasing absorption phase, mean plasma concentrations remain constant between 30.9 and 37.8 ng/ml for an 8 hour period. Additionally, the plasma concentration of acyclovir is now maintained above the minimal inhibitory concentration (MIC) during 16 hours. From the control tablet results, the relative bioavailability of the acyclovir released in the bioadhesive carrier could be calculated. This bioavailability was 35%, but for a dose that was two times less than the control. When calculated with the same dosage as the control, the bioavailability is 70%.

This example proves that the systemic transfer of acyclovir may occur by the transmucosal route, following the impregnation of the strong vascular oral mucosis or by oral route, following the swallowing of saliva enriched in solubilized acyclovir.

Example 6

Evaluation of the Acyclovir Saliva Concentration

Figure 5:
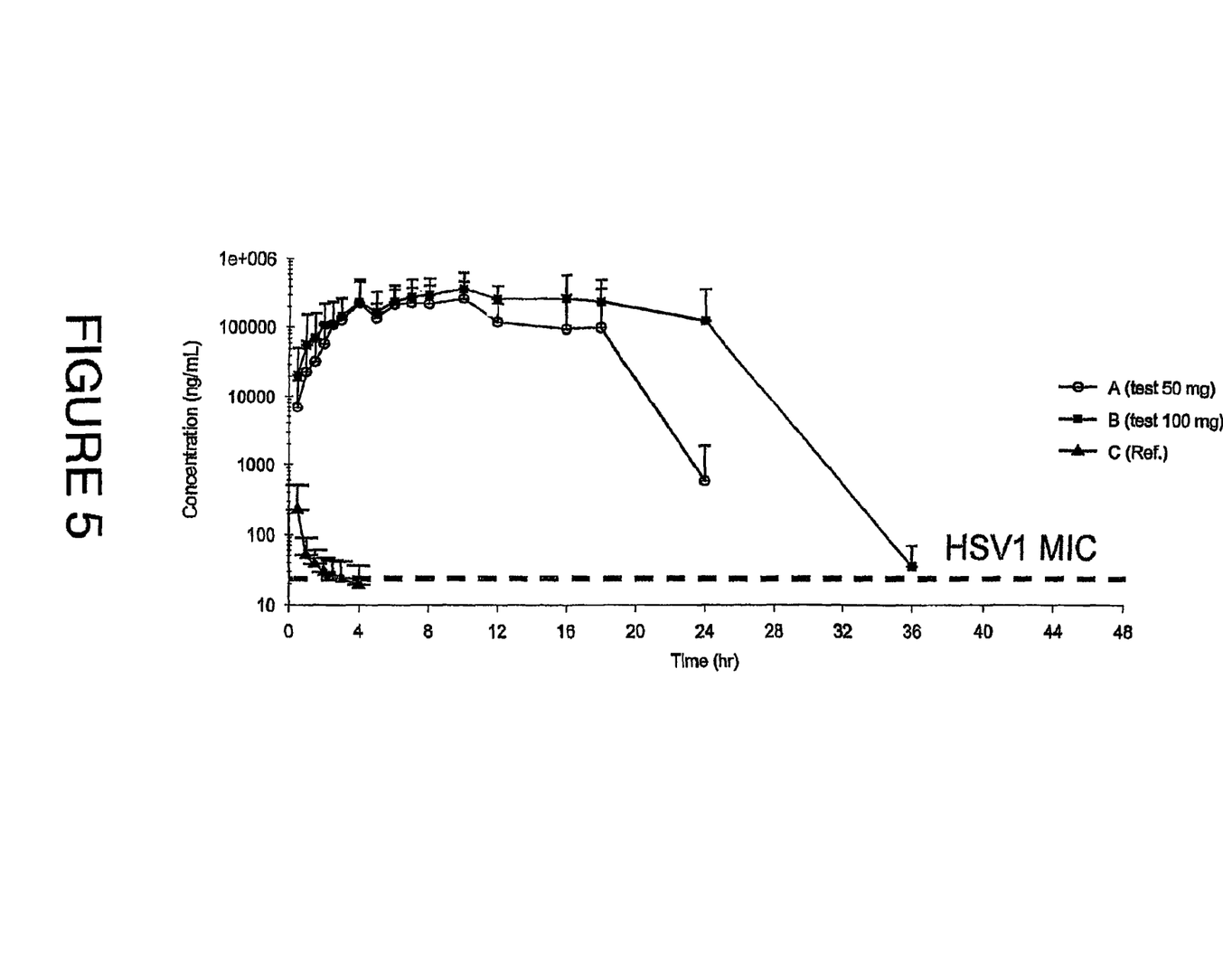
FIG. 5 is a graph showing the concentration of acyclovir in the saliva over time in hours using the bioadhesive slow release carrier of the present invention compared with that of an oral acyclovir tablet.

FIG. 5 illustrates the acyclovir salivary concentration profiles obtained either with the control tablet or with the bioadhesive slow release carrier according to the present invention. As seen in FIG. 5, when the control tablet is administered, the acyclovir appeared in the saliva around 30 minutes after administration, with a peak corresponding to a maximal concentration of 112 ng/ml. The acyclovir saliva concentration remains higher than the minimal inhibitory concentration (MIC) for 4 hours, but decreases quickly after the peak to become undetectable 10 hours after administration.

To the contrary, the bioadhesive slow release carrier of the present invention had very high levels of acyclovir saliva concentrations, even after the first sample taken at 30 minutes after administration. For instance, the saliva concentration of acyclovir was estimated at 6.8 µg/ml after administration of the 50 mg bioadhesive slow release carrier, and at 20 µg/ml after administration of the 100 mg bioadhesive slow release carrier after 30 minutes.

The acyclovir concentrations remained very high during 24 hours to 36 hours, with maximum concentration values of 387 µg/ml and 471 µg/ml respectively for the 50 and 100 mg bioadhesive slow release carriers. This demonstrated that the bioadhesive slow release carriers of the present invention permit the liberation of acyclovir very quickly (30 minutes) and for a long duration of time (36 hours) at the site of the herpes simplex virus-1. These concentrations are much more higher than the acyclovir minimal inhibitory concentration (MIC) required to treat herpes simplex virus-1, since they are respectively 17,000 (for the 50 mg carrier) to 21,000 (for the 100 mg carrier) times greater than the required minimal inhibitory concentration (MIC).

Furthermore, the bioadhesive carrier of the invention reaches a AUC/MIC (area under the curve/minimal inhibitory concentration) ratio of 103,000 to 216,000 in local saliva, while the instant release carrier only provides an AUC/MIC ratio of 8. These exceptionally high ratios demonstrate the very high presence of acyclovir in the saliva, which is at a close proximity to the infection site and therefore favours considerably its local efficiency.

Taken together, these results demonstrate that the acyclovir bioadhesive slow release carrier of the invention favours a very early and sustained release of the acyclovir in the virus reservoir site. Furthermore, the very important amounts of acyclovir in saliva may contribute to limit intra and inter-individual contamination, since it is well known that the virus reservoir potential of saliva plays a key role in the viral spread.

Example 7

Evaluation of the Acyclovir Labial Concentration

Figure 6:
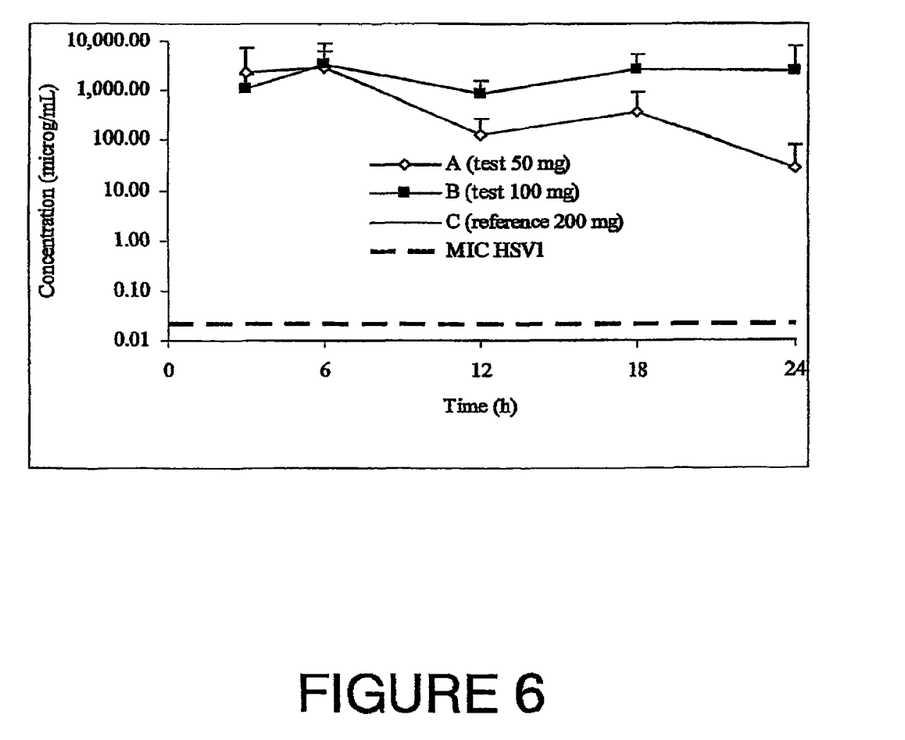
FIG. 6 is a graph showing the concentration of acyclovir on the lips, over time in hours using the bioadhesive slow release carrier of the present invention compared with that of an oral acyclovir tablet.

As disclosed in FIG. 6, acyclovir is not detectable in the labial samples after administration of the control tablet.

To the contrary, when the acyclovir bioadhesive slow release carrier of the present invention was administered, the amount of acyclovir measured on the lips reached concentrations as high as 1 mg/ml. This strong presence of acyclovir on labial sites is maintained during at least 24 h.

The results presented herein thus demonstrate that the carriers according to the invention favour the persistence of very high amounts of acyclovir on the lips i.e., at the expression site of the disease. This implies an increased pressure exerted against the HSV-1 virus, especially at the epidermic level, and suggests a greater efficiency of acyclovir against herpes labialis.

Example 8

Preparation of the Bioadhesive Slow Release Carrier with Different Bioadhesive Polymer 50 mg of acyclovir, 15% by weight microcrystalline cellulose and 4.5% by weight of sodium lauryl sulfate were weighed and sieved with a 0.7 to 2 mm sieve before premixing in a blender to provide the "initial mix."

At the same time, 0.4% by weight polyvinylpyrrolidone was dissolved purified water: The resulting solution was added to the initial mix and further stirred. The wetted mixture was then granulated using a pharmaceutical mixer or granulator such as a planetary mixer or high sear mixer and dried and then calibrated to 500 µm. The resulting pellets formed the "primary granules."

20% of mucoadhesive agent (milk concentrate protein or pea protein or carbopol 974 or chitosan), 15% hypromellose, 1% magnesium stearate and 0.4% of colloidal silica were weighed and sieved using a 500 µm sieve. These ingredients were then added to the primary granulation to form the "final blending" mixture. The final blending mixture was then compressed using a tablet press such as a rotative press to produce the compressed carriers according to the invention.

The size of the tablets was about 8 mm in diameter. The dimension was chosen to be comfortable in the canine fossa.

The above-described method was suitable for the production of compressed carrier batches ranging from 2 to 23 kg.

Example 9

In Vitro Evaluation of the Adhesion-Ability of the Acyclovir Bioadhesive Slow Release Carrier The adhesion ability of the bioadhesive slow release carrier according to the example 8 was measured using a texturometer equipment. The acyclovir carrier was fixed on a plastic probe. The probe came down to the immerged stainless bench, stopped, and then came up.

Adhesion ability was expressed as the "adhesion force" (g), the maximum force needed to separate the tablet, fixed on the probe, from the stainless central parts.

Figure 7:
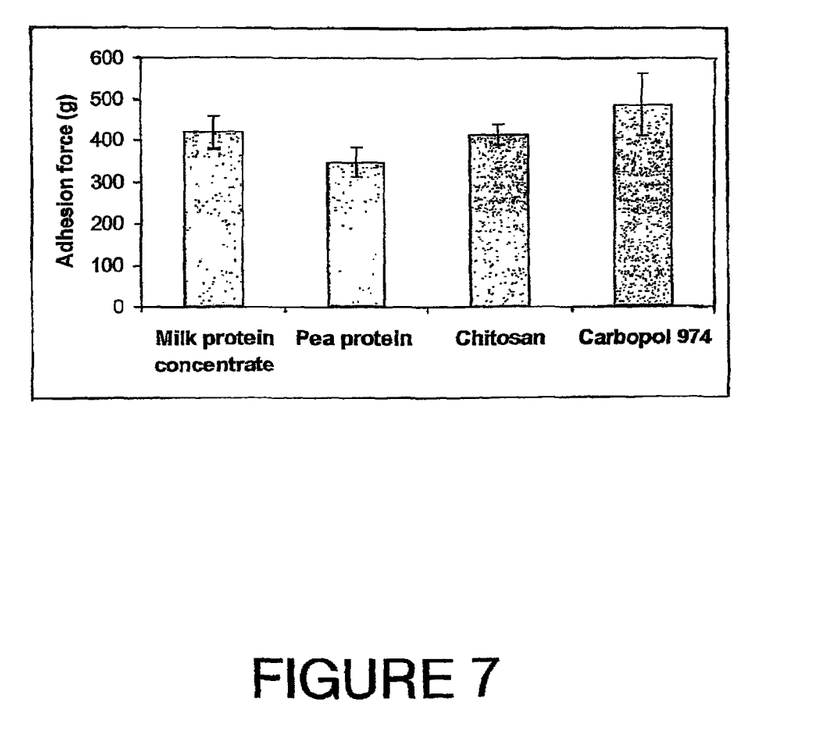
FIG. 7 is a graph showing the adhesion force of the bioadhesive slow release carrier of the present invention using different bioadhesive agents.

The results of the adhesion force for different mucoadhesive agent are presented in FIG. 7.

The results have shown that the different mucoadhesive agents are able to confer similar adhesive properties.

Example 10

In Vivo Evaluation of the Adhesion-Lasting of the Acyclovir Bioadhesive Slow Release Carrier To evaluate the adhesion time of the bioadhesive slow release carrier according to the present invention, this acyclovir carrier was applied on 12 healthy volunteers inside the upper lip. The presence of the carrier was checked at various times until 48 hours. The volunteers were checked on a regular basis for the loss of their carrier just until 24 hours after application. The results of this evaluation are disclosed in the following Table 1.

TABLE 1

| | ADHESION TIME (hours) | |
|---|---|---|
| | 50 mg carrier | 100 mg carrier |
| Median | 14 | 18 |
| Minimum | 6 | 10 |
| Maximum | 18 | 24 |

These results demonstrate that the carrier adhesion is completely compatible with a "once-daily" form of administration. Indeed, as long as the carrier remains at the application site, acyclovir is locally released in close proximity to the aimed infection site. Therefore, the acyclovir bioadhesive slow release carrier obtained with the method disclosed in Example 1 now renders possible the "once-daily" local administration of acyclovir, while achieving efficient locoregional concentrations of the active principle with respect to the MIC.

Example 11

Preparation of the Bioadhesive Slow Release Carrier with Fentanyl 2,000 µg of fentanyl citrate, 30% by weight microcrystalline cellulose and 2% by weight of sodium lauryl sulfate are weighed and sieved using a 0.7 to 2 mm sieve, before premixing in a blender to provide the "initial mix."

At the same time, 0.5% by weight polyvinylpyrrolidone is dissolved in purified water: The resulting solution is added to the initial mix and further stirred. The wetted mixture is then granulated using a pharmaceutical mixer or granulator such as a planetary mixer or highsear mixer, and dried and then calibrated to 500 µm. The resulting pellets form the "primary granulation."

30% milk concentrate protein, 20% hypromellose, 0.2% magnesium stearate and 0.2% of colloidal silica are weighed and sieved using a 500 µm sieve. These ingredients are then added to the primary granulation to form the "final blending" mixture. The final blending mixture is then compressed using a tablet press such as a rotative press to produce the compressed carriers according to the invention.

The same procedure as above is followed to prepare a 800 µg dose of fentanyl.

Example 12

In Vivo Evaluation of the Adhesion-Lasting of the Fentanyl Bioadhesive Slow Release Carrier To evaluate the adhesion time of the bioadhesive slow release carrier according to the present invention, this fentanyl carrier will be applied on 12 healthy volunteers inside the upper lip following the same procedure as in Example 8. The results of this evaluation are set forth in the following Table 2.

TABLE 1

| | ADHESION TIME (hours) | |
|---|---|---|
| | 800 µg carrier | 2,000 µg carrier |
| Median | 20 | 24 |
| Minimum | 17 | 19 |
| Maximum | 36 | 38 |

Example 13

Preparation of the Bioadhesive Slow Release Carrier Using Three Active Principles Following Example 1, the same bioadhesive slow release carrier is prepared using 70 mg acyclovir, 80 µg fentanyl and 5% by weight pilocarpine. To evaluate the adhesion of this carrier, the same procedure is undertaken as in Example 8. The resulting adhesion time is similar to that in Example 10.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A prolonged release mucoadhesive formulation comprising:
   an antiviral agent selected from acyclovir, valacyclovir, gancyclovir, and zidovudin;
   a diluent;
   an alkali metal alkyl sulfate;
   a binding agent;
   at least one bioadhesive polymer that allows the formulation to adhere to the oral mucosa following administration to a human patient; and
   at least one sustained release polymer;
   wherein the formulation is configured to release the antiviral agent to the oral mucosa from 30 minutes to at least 15 hours following administration;
   wherein the formulation comprises primary granules which comprise the antiviral agent, the diluent, the alkali metal alkylsulfate, and the binding agent; and
   wherein the bioadhesive polymer is dispersed in the formulation.

2. The formulation of claim 1, which comprises no more than 5% by weight of a polyvinylpyrrolidone.

3. The formulation of claim 1, wherein the bioadhesive polymer is not in the primary granules.

4. The formulation of claim 2, wherein the bioadhesive polymer is not in the primary granules.

5. The formulation of claim 1 or claim 2, wherein the alkali metal alkyl sulfate is present in an amount between 2% to 6% by weight.

6. The formulation of claim 1 or claim 2, wherein the binding agent is in an amount between 0.5% and 5% by weight.

7. The formulation of claim 1 or claim 2, which comprises between 0.5% and 5% by weight of a polyvinylpyrrolidone.

8. The formulation of claim 1 or claim 2, wherein the bioadhesive polymer is natural proteins.

9. The formulation of claim 8, wherein the natural proteins are natural milk proteins.

10. The formulation of claim 1 or claim 2, wherein said antiviral agent is acyclovir.

11. The formulation of claim 10, which is capable of delivering the acyclovir to the oral mucosa for a period of at least 20 hours.

12. The formulation of claim 10, wherein the acyclovir is in an amount between 50 mg and 100 mg.

13. The formulation of claim 1 or claim 2, which comprises:
   10 mg to 200 mg of acyclovir,
   1% to 75% by weight of microcrystalline cellulose,
   2% to 10% by weight of sodium lauryl sulfate,
   0.5% to 5% by weight of a polyvinylpyrrolidone,
   10% to 40% by weight of at least one bioadhesive polymer selected from natural milk proteins and mixtures thereof, and
   10% to 40% by weight of hypromellose.

14. The formulation of claim 1 or claim 2, which comprises 50 mg or 100 mg acyclovir and following administration to the oral mucosa provides a salivary concentration of acyclovir that is greater than 22.5 ng/ml for 36 hours.

15. A method of treating a mucosal disease, comprising administering to the oral mucosal of a human patient in need thereof the formulation of any one of claim 1 or claim 2.

16. The formulation of claim 1, wherein the formulation is devoid of starch.

17. The formulation of claim 2, wherein the formulation is devoid of starch.

18. The formulation of claim 1, wherein the predominant fraction of primary granules has a diameter of less than 125 µm.

19. The formulation of claim 2, wherein the predominant fraction of primary granules has a diameter of less than 125 µm.

20. The formulation of claim 1, wherein the at least one bioadhesive polymer is present in 10% to 40% by weight of the formulation.

21. The formulation of claim 2, wherein the at least one bioadhesive polymer is present in 10% to 40% by weight of the formulation.

22. The formulation of claim 20 or claim 21, wherein the bioadhesive polymer is natural proteins.

23. The formulation of claim 22, wherein the natural proteins are natural milk proteins.

24. The prolonged release mucoadhesive formulation of claim 1 comprising:
   15% by weight microcrystalline cellulose;
   4.5% by weight sodium lauryl sulfate;
   0.4% by weight polyvinylpyrrolidone;
   20% of at least one bioadhesive polymer selected from milk protein concentrate, pea protein, carbopol 974, and chitosan;
   15% hypromellose;
   1% magnesium stearate;
   0.4% colloidal silica; and
   50 mg of acyclovir.

25. The formulation of claim 24, wherein the bioadhesive polymer is milk protein concentrate.

26. The prolonged release mucoadhesive formulation of claim 1 comprising:
   15% by weight microcrystalline cellulose;
   4.5% by weight sodium lauryl sulfate;
   0.4% by weight polyvinylpyrrolidone;
   20% milk protein concentrate;
   15% hypromellose;
   1% magnesium stearate;
   0.4% colloidal silica; and
   100 mg of acyclovir.

27. A method of treating a mucosal disease, comprising administering to tho oral mucosal of a human patient in need thereof the formulation of claim 5.

28. A method of treating a mucosal disease, comprising administering to the oral mucosal of a human patient in need thereof the formulation of claim 10.

* * * * *